United States Patent [19]

Günther

[11] Patent Number: 4,496,486
[45] Date of Patent: Jan. 29, 1985

[54] METHOD FOR THE PREPARATION OF PHOSPHATIDYL CHOLINE OF LOW OIL CONTENT

[75] Inventor: Bernd-Rainer Günther, Bergheim, Fed. Rep. of Germany

[73] Assignee: A. Nattermann & Cie. GmbH, Cologne, Fed. Rep. of Germany

[21] Appl. No.: 480,480

[22] Filed: Mar. 30, 1983

Related U.S. Application Data

[63] Continuation-in-part of Ser. No. 269,805, Jun. 3, 1981, abandoned.

[30] Foreign Application Priority Data

Jun. 25, 1980 [DE] Fed. Rep. of Germany ....... 3023814

[51] Int. Cl.³ .............................. A23J 7/02; C07F 9/10
[52] U.S. Cl. .................................. 260/403; 260/428.5
[58] Field of Search .................. 260/403, 412.4, 412.8, 260/428.5, 403

[56] References Cited

U.S. PATENT DOCUMENTS

| | | | |
|---|---|---|---|
| 2,090,537 | 8/1937 | Lund | 260/403 |
| 2,356,382 | 8/1944 | Christiansen | 260/403 |
| 3,652,397 | 3/1972 | Pardun | 260/403 |
| 3,869,482 | 3/1975 | Wolfe | 260/403 |
| 4,221,731 | 9/1980 | Short et al. | 260/403 |
| 4,235,793 | 11/1980 | Betzing | 260/403 |

FOREIGN PATENT DOCUMENTS 43018  1/1982  European Pat. Off. ............ 260/403

OTHER PUBLICATIONS

Tokunaga et al., "Chem. Abstracts", vol. 55, (1961), 6736b, Abstract of Japanese 8324, 7/1/60.

*Primary Examiner*—Anton H. Sutto
*Attorney, Agent, or Firm*—Burns, Doane, Swecker & Mathis

[57] ABSTRACT

An improved method is provided for the preparation of phosphatidyl choline having a low oil content. An alcohol and oil-containing phosphatide solution is admixed with an amount of water sufficient to cause oil present therein to separate from the solution. The oil is removed from the solution and a phosphatidyl choline fraction recovered which is substantially oil-free.

10 Claims, No Drawings

METHOD FOR THE PREPARATION OF PHOSPHATIDYL CHOLINE OF LOW OIL CONTENT

CROSS-REFERENCE TO RELATED APPLICATIONS

This application is a continuation-in-part of application Ser. No. 269,805, filed June 3, 1981 now abandoned.

BACKGROUND OF THE INVENTION

Phytogenic crude phosphatides (e.g., derived from soybeans, peanuts, sunflowers or rape) comprise mixtures of about 30–40 percent of neutral oil and free fatty acids, about 5–10 percent of mono-, di-, or polysaccharides, about 50–60 percent of phosphatides and about 1–2 percent of sterols, waxes, amino acids and peptides. The phosphatide part usually consists of a mixture of phosphatidyl cholines, phosphatidyl ethanolamines, phosphatldyl inosites, phosphatidyl serines, phosphatide acids, N-acylcephalin and lysophosphatides.

Phosphatides are employed in large volumes in the food, cosmetic and pharmmaceutical industries. As a rule, a highly purified, oil-free phosphatidyl choline is required for use in the pharmaceutical industry. In order to obtain this degree of purity, it is imperative to remove the oil from the crude phosphatide. By this removal of oil, undesirable odorants and colorants are removed at the same time. The high purified, oil-free phosphatidyl choline is generally extracted from phytogenic phosphatides by means of a three-step proccss.

The first step comprises the acetonic removal of oil from the crude phosphatide to produce a product comprised of about 28–32 percent phosphatidyl choline and a maximum oil content of about 2.5 percent (See, for example, German Auslegeschrift No. 1 053 299; U.S. Pat. No. 3,268,335; German Auslegeschrift No. 1 047 597).

The second step comprises ethanolic extraction of the phosphatides to provide a product comprised of about 48–52 percent of phosphatidyl choline and a maximum oil content of about 2.5 percent. (See, for example, U.S. Pat. No. 2,945,869; U.S. Pat. No. 2,724,649).

In the third step the ethanolic extract phase of the second step is subject to treatment with aluminum oxide (usually by column-type chromatography) to produce a product comprising about 90–95 percent of phosphatidyl choline and a maximum oil content of about 2.5 percent. (See, for example, German Auslegeschrift No. 1 053 299).

This three-step process is very involved and expensive. It is further disadvantageous in that the two first steps require two different solvents (acetone and ethanol). A further drawback of the acetonic oil removal is the formation of acetone by-products such as mesityl oxide, diacetone alcohol, phorone, etc. which may only be present in small quantities but are undesirable because of their toxicity and their distinctive odor.

The method of the present invention overcomes the problem (previously unsolved by the prior art) of providing a simple, preferably single-step, inexpensive process for the production of an "oil-free" (i.e., oil content at most 2.5 percent by weight) phosphatide mixture having a high phosphatidyl choline content (48–52 percent) at high yields of phosphatidyl choline. Such a product may then be converted with the smallest possible quantity of aluminum oxide to a highly purified phosphatidyl choline.

As is described in the German Auslegeschrift No. 1 492 952 and the publication by A. Liebing, Seife-Ole-Fette-Wasche, 1972, Vol. 98, No. 12, pages 359 to 362, the extraction of crude phosphatides can be carried out with 80–95 percent ethanol. Using 95 percent ethanol, an oil-containing phosphatide fraction is obtained. The residual oil would then have to be removed in a second step by acetonic oil extraction to obtain a substantially oil-free product.

The extraction of crude phosphatides with 80 percent ethanol leads to a phosphatide mixture having an oil content of about 1 percent and a phosphatidyl choline content of only 31 percent. The phosphatidyl choline yield amounts to only 19 percent as shown in the comparative Example 3 hereinafter.

In U.S. Pat. No. 3,869,482, the production of phosphatides from animal organs is described. The production of phosphatides from animal organs presents problems of a different nature than does the production of phytogenic phosphatides. The problematic nature presented by the removal of the high oil content is only met in treating phytogenic phosphatides. Furthermore, the disclosed method involves a three-step process in which, in the individual purifying steps, alcohol as well as chloroform or benzene and petroleum ether are required.

U.S. Pat. No. 4,221,731 describes a separation of the phosphatides with the aid of a ternary mixture of hexane or benzene, alcohol and water.

U.S. Pat. No. 4,235,793 describes the production of an oil-containing phosphatide. Through the extraction of crude phosphatides with 85–95 percent ethanol, an ethanol phase is obtained which contains phosphatidyl choline and oil. In this case, no separation of oil and oil-free phosphatides occurs.

U.S. Pat. No. 2,090,537 uses as a starting material a lecithin which contains at least 58 to 78 percent of water. As can be seen from the disclosure of this patent, a separation into three phases does indeed occur, but as is mentioned at column 2, lines 15–25, all three phases still contain oil. As demonstrated in comparative Example 6 hereinafter wherein the disclosed process was reproduced, a product with an oil content of 12 percent was obtained. Therefore, the reference in claim 4 of that patent to "substantially fat- and oil-free" can only mean a partial rather than substantially complete oil removal. The product has a phosphatidyl choline content of about 25 percent.

In U.S. Pat. No. 2,356,382, a crude phosphatide sludge is used as the starting material which in itself contains large amounts of water. The process carried out according to this patent does not provide an oil-free phospnatide fraction since all fractions that are obtained still contain about 10 percent of oil in addition to the phosphatides. Example 7 hereinafter demonstrates that a clear separation of oil and phosphatidyl choline is not possible by carrying out the process of this patent.

The object of the invention of U.S. Pat. No. 3,652,397 is the production of a lyso crude phosphatide sludge (raw phosphatide with 44 percent of water) and pancreatine. According to the patent, the fatty acids that are released by the lyso formation and in part the oil from the reactive mixture are removed by addition of isopropanol. (See Comparative Example 8 hereinafter).

German Pat. No. 261 212 and U.S. Pat. No. 1,001,247 describe a process for the precipitation of phosphatides and oil from ethanolic oil-containing crude phosphatide extracts by the addition of water.

DETAILED DESCRIPTION OF THE PRESENT INVENTION

Now it has been surprisingly and unexpectedly discovered that a small addition of water to the alcoholic phosphatide-containing solution which is obtained by the extraction of crude phosphatides with an alcohol achieves a substantially complete separation of the oil (i.e., the triglycerides) from the alcoholic solution, such that the oil component can be separated without precipitation of the phosphatidyl choline, as would be expected from the disclosure of German Pat. No. 261 212 and U.S. Pat. No. 1,001,247. In spite of the presence of the phosphatides that act as emulsifiers, the desired phase separation occurs. Substantially oil-free phosphatidyl choline can thus be obtained in high yields.

According to German Pat. No. 1 492 952, it is known in principle how to obtain oil-free phosphatide fractions by extraction of crude phosphatide with 80 percent ethanol. In this case, the low phosphatidyl choline yield (19 percent of the theoretical value) and the low phosphatidyl choline content (31 percent) are very disadvantageous.

According to the state of the art, it was not thought to be reasonable to add water to the alcoholic extract phase because precipitation of the phosphatides and the oil was to be expected. It was all the more surprising that by the process according to the present invention, an oil-free phosphatide fraction with at most about 2.5 percent oil, about 51 percent of phosphatidyl choline and a very high phosphatidyl choline yield of about 35 percent can be obtained.

Therefore, according to the invention, the alcoholic, oil-containing phosphatide solution is mixed with 10–20 volume percent of water with respect to the alcoholic solution, the oil sediment is separated and the phosphatidyl choline is isolated from the aqueous alcohol phase. This isolation can result from volatilization of the aqueous alcohol, or by an adsorption of the phosphatidyl choline on aluminum oxide and elution with alcohol. Advantageously, one not only is able to achieve an oil removal by the choice of the admixed amount of water but also controls the phosphatidyl choline: phosphatidyl ethanolamine ratio to obtain phosphatidyl ethanolamine-poor or -free phosphatidyl choline fractions.

Commercial phytogenic crude phosphatides such as, e.g., soybean, peanut, sunflower or rape may be used to carry out the present invention. The crude phosphatide is extracted with a low molecular weight aliphatic alcohol such as, e.g. methanol, ethanol, etc. and preferably with 94–96 percent ethanol in a weight ratio of 1:1–1:5, and preferably 1:2–1:3, raw phosphatide: alcoholic solution at about 30°–50° C. This extract solution is freed of sediment and the clear alcohol phase is mixed with 10–20 percent by volume of water to precipitate the oil phase. The triglyceride-containing sediment is then separated. The aqueous alcohol phase can now be further purified according to known processes through $Al_2O_3$ stir- or column-type chromatography, as is described in German Auslegeschrift No. 1 047 597. According to the novel method as described herein, the extraction phase can, however, be first treated with aluminum oxide, as described in German Auslegesthrift No. 2 718 797 and then be subjected to an aqueous oil removal as described above.

According to the method of the present invention, a substantially oil-free phosphatidyl choline is obtained in high yield by means of simple manipulative steps.

The invention is additionally illustrated in connection with the following Examples which are to be considered as illustrative of the present invention. It should be understood, however, that the invention is not limited to the specific details of the Examples.

EXAMPLE 1

(a) Soybean crude phosphatide with about 25 percent triglyceride content was continuously extracted at 35° C. with 95 percent by volume aqueous ethanol in a weight ratio of 1:2.5 (crude phosphatide:ethanol). The sediment was separated at room temperature and the ethanol phase evaporated. The extraction yield and composition of the product is set forth below:

| | |
|---|---|
| Extraction yield | 27% by weight |
| Phosphatidyl choline content | 48% |
| Phosphatidyl ethanolamine content | 12% |
| Oil (triglyceride) content | 21% |
| Yield: Phosphatidyl choline 56% based on the crude phosphatide | |

(b) One liter each of the ethanolic extract solution containing 88 grams of solids/liter obtained in part (a) above was mixed at room temperature with varying amounts of water. After separation of the thus-formed sediment, the remaining aqueous ethanol phases were evaporated. The following results were obtained:

| Water added per liter soln (ml) | Phosphatidyl choline content (% by wt) | Phosphatidyl choline: phosphatidyl ethanolamine | Triglyceride content (% by wt) | Phosphatidyl choline yield based on crude phosphatide (% by wt) |
|---|---|---|---|---|
| 75 | 50 | 5:1 | 9 | 48 |
| 175 | 51 | 6:1 | 2 | 35 |
| 225 | 54 | 7:1 | 1 | 31 |
| 400 | 55 | 11:1 | <1 | 11 |

(c) 1.11 liter of an aqueous ethanol phase (solids content 55 grams/liter) prepared according to part (b) above with 175 milliliters of water was charged to a chromatographic column (30 mm diameter, 400 mm height) which is filled with a suspension of 220 grams of $Al_2O_3$ in diluted ethanol. After passing through the column, the solution was washed again with dilute ethanol. The combined ethanol phases were vaporized. A residue of 25 grams of a phosphatldyl ethanolamine- and triglyceride-free residue was obtained which analyzed as follows:

| | |
|---|---|
| Phosphatidyl choline content | 92% by wt |
| Phosphatidyl choline yield based on crude phosphatide | 29% |

EXAMPLE 2

One liter of an ethanolic extract solution (88 grams of solids/liter) obtained according to Example 1(a) above was mixed with 350 grams $Al_2O_3$ for 2 hours at room temperature under agitation. The $Al_2O_3$ was suctioned off and flushed with 95 percent by volume of ethanol (20% triglyceride content in the dry substance). The filtrate was mixed with 175 milliliters of water. The sediment was then separated and the remaining aqueous ethanol phase vaporized. About 44 grams of a phosphatidyl ethanolamine- and triglyceride-free residue were obtained which analyzed as follows:

| | |
|---|---|
| Phosphatidyl choline content | 85% by wt |
| Phosphatidyl choline yield based on crude phosphatide | 46% |

EXAMPLE 3

This comparative example is carried out according to the process of A. Liebing, Seifen-Ole-Fette-Wachse 1972, Vol. 98, No. 12, pages 359–362. This comparative example demonstrates that while prior art methods are sometimes capable of providing a phosphatidyl choline fraction having a low triglyceride content, the overall yield is not acceptable.

Raw soybean phosphatide was continuously extracted at 45° C. with 80 percent by volume of ethanol. The soybean phosphatide-ethanol ratio (wt/wt) was 1:2.5. The sediment formed was separated at room temperature and the ethanol phase evaporated.

| | |
|---|---|
| Extract yield | 14% by wt. |
| Phosphatidyl choline content | 31% |
| Phosphatidyl ethanolamine content | 4% |
| Triglyceride content | 1% |
| Phosphatidyl choline yield based on crude phosphatide | 19% |

EXAMPLE 4

A phosphatide fraction was produced according to the method described in Example 1 of German Pat. No. 1 492 952. The alcohol-soluble fraction was evaporated. The residue contained 15 percent by weight of triglycerides.

EXAMPLE 5

(a) 250 grams of soybean raw phosphatide were extracted at 50° C. with 1000 grams of methanol. The sediment was separated at room temperature and the methanol phase evaporated.

| | |
|---|---|
| Extract yield | 34% by wt. |
| Phosphatidyl choline content | 46% |
| Phosphatidyl ethanolamine content | 15% |
| Triglyceride content | 10% |
| Phosphatidyl choline yield based on crude phosphatide | 68% |

(b) One liter of a methanolic extract solution (70 grams of solids/liter) obtained according to part (a) above was mixed with 100 milliliters of water. After separation of the sediment formed, the aqueous methanol phase was evaporated. A resiiue of 61 grams of residue was obtained which analyzed as follows:

| | |
|---|---|
| Phosphatidyl choline content | 48% by wt. |
| Phosphatidyl ethanolamlne content | 9% |
| Triglyceride content | <1%. |

EXAMPLE 6

The process according to U.S. Pat. No. 2,090,537 was repeated by adding 20 grams of soybean crude phosphatide (phosphatidyl choline content 18 percent, oil content 29 percent) to a mixture of comprised of 15 percent ethanol (96 percent) and 65 grams water at 160° F. The mixture was stirred intensively for 1 hour at 160° F., cooled without stirring to room temperature, and the lower phase separated. The lower phase was evaporated and the phosphatidyl choline- or oil content, respectively, determined and set forth below:
Solids Yield: 11 grams
Phosphatidyl choline content: 25% by wt.
Oil content: 12% by wt.

EXAMPLE 7

The process according to U.S. Pat. No. 2,356,382 was repeated. In the patent, peanut phosphatide sludge (water content estimated to be about 30–50 percent) was used, while in this Example the raw material comprised soybean phosphatide sludge.

(a) Soybean crude phosphatide sludge with 35 percent water was stirred with 5, 10, 15 and 20 percent ethanol at 60° C. No phase separation occurred.

(b) Soybean crude phosphatide sludge with 45% water was stirred with 5, 10, 15 and 20 percent ethanol at 60° C. Partial phase separation occurred. The upper phase was enriched in oil. The desired lower phase showed a phosphatidyl choline content of 24 percent and an oil content of 10 percent.

EXAMPLE 8

The process according to U.S. Pat. No. 3,652,397, was repeated by calculation, with the following results being obtained:
lyso raw phosphatide (dry substance) 200 grams (approx. 35 percent oil or 70 grams oil). The initial oil content in raw phosphatide corresponds to acetone-soluble content, usually 35 percent.

The lyso raw phosphatide after treatment with isopropanol water comprised 156 grams (200 g − 44 g = 156 g) of which 26 grams are oil. The final product thus contains 17 percent by weight of oil.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. A method for the preparation of a substantially oil-free phosphatidyl choline fraction from an oil-containing phosphatide fraction comprising admixing a solution comprised of an alcohol and an oil-containing phosphatide resulting from the alcohol extraction of said phosphatide with between about 10 and 20 percent by volume of water based on said solution to cause oil present therein to separate from said solution, removing said oil from said solution and recovering a substantially oil-free phosphatidylcholine fraction from said solution.

2. The method of claim 1 wherein said phosphatide fraction is derived from soybean phosphatides.

3. The method of claim 1 wherein said alcohol-containing solution comprises a low molecular weight aliphatic alcohol.

4. The method of claim 3 wherein said alcohol is selected from the group consisting of methanol, and ethanol.

5. The method of claim 4 wherein said alcohol comprises ethanol.

6. The method of claim 1 wherein said oil comprises triglycerides.

7. The method of claim 1 wherein said substantially oil-free phosphatidyl choline fraction is recovered by evaporation.

8. The method of claim 1 wherein said substantially oil-free phosphatidylcholine fraction comprises less than about two percent by weight of oil.

9. The method of claim 1 wherein said alcohol comprises a 94–96 percent alcohol.

10. The method of claim 9 wherein said alcohol is ethanol.

* * * * *